United States Patent [19]
Kakimi et al.

[11] Patent Number: 4,650,769
[45] Date of Patent: * Mar. 17, 1987

[54] MICROCAPSULES FOR IMMUNE RESPONSE

[75] Inventors: Fujio Kakimi; Hiroharu Matsukawa, both of Shizuoka; Yutaka Akiyoshi; Shinzo Kobayashi, both of Tokyo, all of Japan

[73] Assignee: Fuji Photo Film Co., Ltd., Kanagawa, Japan

[*] Notice: The portion of the term of this patent subsequent to Aug. 3, 1999 has been disclaimed.

[21] Appl. No.: 585,634

[22] Filed: Mar. 8, 1984

Related U.S. Application Data

[63] Continuation of Ser. No. 281,454, Jul. 8, 1981.

[30] Foreign Application Priority Data

Jul. 9, 1980 [JP] Japan ................................. 55-93405

[51] Int. Cl.$^4$ .................. G01N 33/546; G01N 33/544
[52] U.S. Cl. ..................................... 436/533; 436/534; 436/535; 436/823; 436/824; 436/829; 428/402.2
[58] Field of Search ............... 436/518, 532, 533, 534, 436/535, 823, 824, 829; 252/315.1; 428/402.2

[56] References Cited

U.S. PATENT DOCUMENTS

| 3,857,931 | 12/1974 | Hager | 424/12 |
| 4,021,364 | 5/1977 | Spelser | 424/89 X |
| 4,193,983 | 3/1980 | Ullman | 424/3 X |
| 4,254,096 | 3/1981 | Monthory et al. | 436/532 |
| 4,255,411 | 3/1981 | Lim | 424/12 X |
| 4,342,739 | 8/1982 | Kakimi et al. | 436/518 |
| 4,349,530 | 9/1982 | Royer | 424/22 |
| 4,362,697 | 12/1982 | Tabb et al. | 435/805 |
| 4,559,303 | 12/1985 | Aotani et al. | 436/823 |

Primary Examiner—Christine M. Nucker
Attorney, Agent, or Firm—Sughrue, Mion, Zinn, Macpeak & Seas

[57] ABSTRACT

Microcapsules for effecting an immune response, especially through agglutination reaction, comprise an antigen or antibody bound to functional groups, such as amino groups, carboxy groups, etc., on a wall surface of the microcapsules via cross linking agents, such as polyfunctional isocyanates, isothiocyanates, etc. The antigen or antibody is strongly bound to the wall surface of the microcapsules to thereby achieve excellent detection sensitivity.

16 Claims, No Drawings

MICROCAPSULES FOR IMMUNE RESPONSE

This application is a continuation of application Ser. No. 281,454, filed July 8, 1981.

BACKGROUND OF THE INVENTION

1. Field of the Invention

The invention relates to a microcapsule reagent suitable for immunological response, more particularly to a microcapsule reagent suitable for an antigen-antibody response which provides high sensitivity, is stable and causes non-specific agglutination only with difficulty.

2. Development of the Invention

In order to facilitate an antigen-antibody response of high sensitivity in a simple manner, an immunological agglutination method in which an antigen or antibody is carried on a water-insoluble carrier which causes agglutination based on an antigen-antibody response which can be seen with the naked eye has been employed.

Red blood cells of animals such as chicken, alligators, sheep, etc. have been used as carriers for the antigens or antibodies, and, utilizing these carriers, passive haemagglutination (PHA) has generally been used since this method provides high sensitivity with simple operations. Recently, a method has been used for semi-qualitatively determining the presence or absence of antigens or antibodies very efficiently in a simple manner which is called the microtiter system. However, the microtiter system involves disadvantages, e.g., due to the use of animal-originated carriers, red cell carriers per se are antigenetic and cause specific agglutination to adversely affect the desired antigen-antibody response; further, efficiency is not uniform based on differences between subjects, changes with the passage of time, and cost is high.

A latex agglutination method in which a polystyrene latex is used as a carrier has also been put into practical use. While the disadvantages encountered with the use of animal-originated carriers is eliminated by this method, this method also involves disadvantages, e.g., not only is sensitivity poor as compared to the passive haemagglutination method, but storability over long periods of time is poor because of a weak bond with an antigen or antibody. Further natural agglutination—which is not based on an antigen-antibody response—tends to occur, etc.

In U.S. Ser. No. 110,318 filed Jan. 8, 1980, a method for detecting an antibody or antigen using microcapsules having an antigen or antibody bound to the wall surface thereof via antigen-antibody agglutination is proposed. Further, in order to improve the detection sensitivity of such microcapsules, microcapsule reagents in which specific wall materials such as polyurea, polyurethane, etc., are employed are also proposed. By the use of such microcapsule reagents, improved detection sensitivity is attained, but such systems are not satisfactory from the standpoint of storability over long periods of time.

SUMMARY OF THE INVENTION

It has now been found that by using microcapsules obtained by introducing into the wall surfaces thereof one or more functiona groups an antigen or antibody can be bound to the microcapsules via a cross linking agent in which one group is chemically bound to an antigen or antibody and the other group is bound to the microcapsule wall. As a result, the antigen or antibody is strongly bound to the microcapsules by chemical reaction so that a reagent having excellent storability over long periods of time results. The thus obtained microcapsule reagent is highly stable, especially in that it can withstand freeze-dyring which is a representative of storage for long periods of time.

The term "microcapsule" refers to a microcapsule comprising a wall material having encapsulated therein an oily substance as the core. The term "functional group" refers to a group which has a site for binding an antigen or antibody via a cross linking agent.

DESCRIPTION OF THE PREFERRED EMBODIMENTS

Typical examples of functional groups which are introduced into and chemically bound to the wall surface of a microcapsule include an amino group, a carboxy group, a hydroxy group, a mercapto group, etc.

Introduction of functional groups into the wall surface of the microcapsule in accordance with the present invention can be carried out either using compounds containing functional groups as a wall substance of the microcapsule, or, after preparation of a microcapsule, by subjecting the surface thereof to a chemical treatment as will be later explained.

Chemical treatments include a method for converting a precursor as a wall substance into a substance having the desired functional groups through a chemical reaction, a method for reacting a compound having functional groups with the wall surface of a microcapsule and a method for binding a compound containing functional groups to the wall surface of a microcapsule using a cross-linking agent.

Any compound(s) can be employed as the wall substance(s) for the microcapsule employed in the present invention without any particular limitation so long as they are capable of chemically bonding to an antigen or antibody without inactivating an antigen or antibody and are capable of encapsulation.

The term "wall substance" used herein refers to any wall substance which is generally accepted in the art of microcapsule technology, as seen in U.S. Pat. Nos. 4,087,376, 4,089,802 and 4,100,103, and British Pat. No. 53,170.

Microcapsules employed in the present invention which contain a functional group(s) on the wall surface thereof can be obtained by reacting a polyfunctional compound (wall material), such as a polyfunctional isocyanate, a polyfunctional isothiocyanate, a polyfunctional acid chloride, a polyfunctional epoxy compound, etc., with a substance having the desired functional group(s), thus forming a wall.

Amino-containing substances employed for preparing microcapsules are those that contain at least two amino groups in one molecule thereof and thus contain about 20 to about 60 mol%, same basis. Typical examples of such amino-containing substances include a polyfunctional amino compound (e.g., ethylenediamine, hexamethylenediamine, cyclic amines such as Epomate (tradename, made by Ajinomoto Co., Ltd.; amine hardner), etc.) an amino acid (arginine, lysine, cystine, etc.), etc.

Carboxy- and/or hydroxy-containing compounds employed for preparing microcapsules containing a carboxy and/or hydroxy groups are those that contain at least two carboxy groups, at least two hydroxy groups, or, at least one carboxy and hydroxy groups. A proportion of such carboxy and/or hydroxy functional groups is about 20 to 100 mol%, based upon the total monomer.

Typical examples of carboxy-containing substances include carboxymethyl cellulose, polyacrylic acid, polymethacrylic acid, polystyrene carboxylic acid, etc.

Representative example of hydroxy-containing substance is polyvinyl alcohol (degree of saponification, more than 90%).

Mercapto-containing substances are those that contain at least one mercapto group in one molecule thereof.

Microcapsule having a mercapto group(s) on the wall surface thereof can be prepared by reacting a polyfunctional compound (wall material) such as a polyfunctional isocyanate, a polyfunctional isothiocyanate, a polyfunctional acid chloride, a polyfunctional epoxy compound, etc., with thiourea to form walls and then reducing the thus formed microcapsules at room temperature.

Microcapsules containing a mercapto group(s) on the wall surface thereof can also be prepared by reacting S-acetylmercaptosuccinic acid hydride with microcapsules containing amino groups on the wall surface thereof.

Microcapsules having carboxy groups on the wall surfaces thereof can be prepared by reacting a polyfunctional compound (wall material) such as a polyfunctional isocyanate, a polyfunctional isothiocyanate, a polyfunctional acid chloride, a polyfunctional epoxy compound, etc., with an ester compound such as a polyacrylate, a polymethacrylate, etc., to form walls and then hydrolyzing the thus formed microcapsules under acidic conditions. The acidic conditions are the same as those set for preparing microcapsules under which the hydrolysis is simultaneously proceeded.

Specific examples of polyfunctional isocyanates used as the wall material include toluene diisocyanate, xylene diisocyanate tolylene diisocyanate, hexamethylene diisocyanate, etc.

Specific examples of polyfunctional isothiocyanates include phenylene diisothiocyanate, ethylene diisothiocyanate, etc.

Specific examples of polyfunctional acid chlorides are 1-hydroxy-2,4-disulfonyl chloride, etc.

Specific examples of polyfunctional epoxy compounds include diepoxybenzene, etc.

Although the polyfunctional compounds used to prepare the wall material are not limited to the above, those as described above are particularly preferred in the invention.

The polyfunctional compound(s) employed to prepare the wall material are generally used in an amount of 5 to 25 wt%, based on an oily core material, and compounds used to introduce the functional group(s) onto the wall surface are used in an amount of 2 to 20 wt%, same basis.

As oily substances which can be used to form the core for microcapsules per the present invention, natural mineral oils, animal oils, plant oils and synthetic oils can be employed in the present invention. These core substances are completely enclosed within the capsule walls and hence do not directly affect the antigen or antibody.

Preferred examples of mineral oils include petroleum, kerosene, gasoline, naphtha, a paraffin oil, etc. Preferred examples of animal oils include fish oil, lard, etc. Preferred examples of plant oils include peanut oil, linseed oil, soybean oil, castor oil, corn oil, etc. Examples of synthetic oils are biphenyl compounds (e.g., isopropyl biphenyl, isoamyl biphenyl), terphenyl compounds (e.g., compounds as described in German OLS No. 2,153,635), naphthalene compounds (e.g., diisopropyl naphthalene, compounds as described in U.S. Pat. No. 4,003,589), alkylated diphenylalkanes (e.g., 2,4-dimethyldiphenylmethane, compounds as described in U.S. Pat. No. 3,836,383), phthalic acid compounds (e.g., diethyl phthalate, dibutyl phthalate, dioctyl phthalate), etc.

Core substances for the microcapsules which can be employed in the present invention are those conventionally used in the microcapsule art and thus not limited to compounds described above.

In order to improve contrast to agglutination, oil-soluble dyes can also be incorporated into the core material in an amount of 0.05-10 wt%, preferably 0.1-5 wt%. While not overly limited, examples of useful oil-soluble dyes include dyes having Color Index Nos. 12010, 12150, 12715, 12716, 13900, 26100, 26105, 26110, 26125, 27291, 45710, 60505, etc.

The core materials for the microcapsule of this invention can also contain marking substances such as an isotope, a fluorescent substance, a magnetic substance, a ultraviolet substance, etc., in an amount of 0.05-10 wt%, preferably 0.1-5 wt% (see U.S. Ser. No. 110,318, filed Jan. 8, 1980, for examples of such materials).

Methods for preparing microcapsules used in this invention are not particularly limited and conventional methods can be employed, for example, as described in T. Kondo, MICROENCAPSULATION— New Technique and Application, Techno Books (1979), U.S. Pat. Nos. 4,087,376, 4,089,802 and 4,100,103 and British Pat. No. 53,170, T. Kondo, MICROCAPSULE, Sankyo Publishing Co., Ltd., Tokyo(1972), Asaji Kondo, MICROCAPSULE, Nikkan Kogyo Press, Tokyo(1970), etc.

It is preferred that the specific gravity of mircocapsules used in the present invention ranges from about 0.80 to about 1.20 on a dry basis, and such can be modified by appropriately choosing the core substance based upon criteria which are conventional and thus obvious to one skilled in the art.

It is preferred that an average particle size of the microcapsules be in a range of from 0.1 to 30 microns, more preferably 0.5 to 10 microns, but not particularly limited thereto. While it varies depending upon a core size used, it is preferred that an average wall thickness of the microcapsules be in a range of from about 100 to about 300 nm.

The concentration of the functional group(s) on the wall surface of the microcapsule is conventionally determined by a fluorescence measurement method.

In the case that the functional groups are amino groups, the intensity of a fluorescent substance formed by reaction of the amino groups and fluorescamine is measured at 475 nm using an excitation wavelength of 390 nm using, e.g., with a Hitachi Fluorospectrometer Model 650 (tradename, made by Hitachi Co., Ltd.), in accordance with the fluorescamine method described in Kiyoshi Sugawara and Masami Soejima, *TAMPAKU-SHITSU*-NO-TEIRYOHO (Quantitative Analysis of Proteins), page 179 (1979), published by Gakkai Shuppan Center, Tokyo. Using a calibration curve separately prepared using glycine, quantitative analysis can easily be prepared.

In the case where the functional groups are carboxyl groups, 1-ethyl-3-(3-dimethylaminopropyl)carbodiimide hydrochloride is firstly reacted with the carboxyl groups; the remaining carbodiimide is washed off. Thereafter, ethylene diamine is reacted with the resulting reaction product. After the remaining ethylene diamine is removed by washing, amino groups thus converted are quantitatively determined in accordance with the aforesaid fluorescamine method.

When the functional groups are hydroxy groups, the hydroxy groups are converted into amino groups in a manner similar to the case of the carboxyl functional groups in a conventional manner followed by quantitative determination as for the carboxyl functional groups.

In the case where the functional groups are mercapto groups, quantitative determination is performed in accordance with the silver potential titration method in which a silver sulfide electrode is employed in a silver nitrate solution, with reference to a saturated calomel electrode.

It is advantageous that the functional groups at the wall surface of the microcapsule of the present invention be present in an amount of $10^{-9}$ mol or more, per 1 mg. of the solid components (the wall plus the core) of the microcapsule, preferably ranging from $10^{-9}$ to $10^{-5}$ mol, same basis.

To bind an antigen or antibody with the functional groups at the wall surface of a microcapsule in the present invention, a cross linking agent is employed; in this case, there are three basic embodiments as described below.

A first embodiment comprises firstly binding a cross linking agent with the functional groups on the wall surface of a microcapsule and then reacting an antigen or antibody with the resulting reaction product to thereby bind the functional groups at the wall surface of the microcapsule with an antigen or antibody via the cross linking agent.

A second embodiment comprises firstly reacting an antigen or antibody with a cross linking agent and then binding the resulting compound with the functional groups at the wall surface of a microcapsule.

A third embodiment comprises forming a system, e.g., a mixture, of an antigen or antibody, a cross linking agent and a microcapsule and simultaneously causing reaction of the antigen or antibody with the functional groups at the wall surface of the microcapsule through the cross linking agent.

Typical examples of cross linking agents which can be employed to bind an antigen or antibody to the functional groups at the wall surface of a microcapsule therethrough include: when the functional groups are amino groups—dialdehydes such as glutaraldehyde; diisocyanates such as toluene-2,4-diisocyanate; dithioisocyanates such as p-phenylenedithioisocyanate; imide esters such as diethyl maloneimidate; disulfonyl chlorides such as 1-hydroxy-2,4-disulfonyl chloride; halonitrobenzenes such as p,p'-difluoro-m,m'-dinitrophenylsulfonic acid, etc.; when the functional groups are carboxyl groups—water-soluble carbodiimides such as 1-ethyl-3-(3-dimethylaminopropyl)carbodiimide hydrochloride, 1-cyclohexyl-3-(2-morpholinyl-4-ethyl)-carbodiimidomethyl-p-toluenesulfonic acid; isoxazolium salts such as N-ethyl-5-phenylisoxazolium-3'-sulfonic acid; alkyl chloroformates such as ethyl chloroformate, etc.; when the functional groups are mercapto groups—N,N'-O-phenylenedimaleimide, m-maleimidobenzoyl-N-hydroxysuccinimide esters, etc. However, the polyfunctional compounds are not particularly limited to those described above.

Representative examples of immunologically active substances which can be bound to the wall surface of a microcapsule in accordance with the present invention to cause an antigen-antibody response include peptide hormones such as hypothalamus hormones (e.g., TRH, LH-RH, somatostatin), hypohysis hormones (e.g., growth hormone, ACTH, $\alpha$-MSH, $\beta$-MSH, lipotropin, prolactin, TSH, TSH-$\beta$, LH, LH-$\beta$, FSH, FSH-$\beta$, $\alpha$-subnit, arginine vasopressin, lysine vasopressin, oxytocin, etc.), calcium metabolism-regulating hormones (e.g., insulin, proinsulin, C-peptide, glucagon, etc.), digestive tract hormones (e.g., gastrin, sectretin, pancreozymin, chlocystokinin, GIP, enteroglucagon, etc.), hormones acting on blood vessels (e.g., angiotensin I, angiotensin II, bradykinins, etc.), placenta hormones (e.g., human chorionic somatomammotropin, human chorionic thyrotropin), non-peptide hormones such as steroids (e.g., cortisol, corticosterone, 11-deoxycortisol, 11-deoxycorticosterone, progesterone, 17-hydroxyprogesterone, pregnenolone, aldosterone, testosterone, dihydrotestosterone, estradiol, estriol, estrone, 2-hydroxyesterone, dehydroepiandrosterone, etc.), thyroid hormones (e.g., thyroxin, 3,5,3'-triiodothyronin, 3,3'5'-triiodothyronin, etc.), prostaglandins (e.g., prostaglandin A, E, F, etc.); substances other than hormones such as drugs (e.g., digoxin, digitoxin, morphine, LSD, gentamycin, amphetamine, nicotine, etc.), cyclic nucleotides (e.g., cyclic AMP, cyclic GMP, cyclic IMP, cyclic UMP, etc.), enzymes (e.g., $C_1$ esterase, fructose 1,6-diphosphatase, alkaline phosphatase, dopamine beta hydroxylase, pepsinogen, etc.), virus specific antigens (e.g., hepatitis B virus, murine sacromaleukemia virus, wooly monkey leukemia virus, avian tumor virus, plant virus, avian C-type virus, treponema pallidum, leptospira, etc.), tumor antigens (e.g., $\alpha$-fetoprotein, CEA, etc.), blood serum proteins (e.g., thyroxin binding globulin (TBG), IgG, IgM, IgA, $\alpha_2$-microglobulin, properdin, anti-Rh antibodies, transferrin, aplipoproptain, fibrinogen degradation products, antihemolytic factor, renin, etc.); rheumatism factor, folic acid, neutrophysin, somatomedin B, nerve growth factor, epidermal growth factor, staphylococcal enterotoxin A and B, type A toxin of chlostridium botulinium, myosin, encephalitogenic basic proteins, substance P, serotonin, conjugated cholyl bile acid, $H_{BS}$-antigen, etc.

Of these immunologically active substances, those which are particularly preferably bound onto the wall surface of the microcapsules in this invention are IgG, IgE, IgA, insulin, $H_{BS}$-antigen, $\alpha$-fetoprotein, human growth hormone, renin, gastrine, LH, FSH, cortisol, angiotensin, ACTH, C-peptide, CEA, glucagone, and aldosterone.

Procedures for binding antigens or antibodies with microcapsule walls in accordance with this invention will now be described in more detail.

The resulting microcapsule slurry is diluted with a saline solution to a 1 to 3% solids content (the core and the wall).

A cross linking agent, e.g., glutaraldehyde, is added to the thus diluted microcapsule slurry in an amount of 0.1 to 50 wt% based on the solids content of the slurry. The resulting mixture is incubated at a temperature(s) of room temperature to 65° C. for 5 to 120 mins. to react the cross-linking agent with the functional groups on the microcapsule walls. Then, residual cross linking agent is removed by washing by means of centrifugal separation.

An antigen or antibody is added to the dispersion in an amount of 0.1 to 25 wt% based on the solids content of the slurry. The mixture is incubated at 37° C. for 30 to 120 mins. to react the antigen or antibody with the remaining functional groups of the glutaraldehyde bound to the microcapsule walls, on the one hand. On the other hand, the functional groups of the glutaraldehyde which are bound to the microcapsule walls at one terminal but remain unreacted at the other terminal are reacted with aglucine solution to completely block unreacted glutaraldehyde functional groups, thus avoiding undesired non-specific immune response.

The diagnostic materials obtained in accordance with the present invention are characterized by extremely high sensitivity in agglutination, by the fact that non-specific agglutination occurs only with extreme difficulty, by the fact that they can be stably stored over long periods of time and easily manufactured with uniform quality on an industrial scale, by the fact that antigens or antibodies therewith can be selected from an extremely wide range, by the fact that an oily substance is employed as the core of the microcapsule which renders encapsulation easier, as compared to the use of a water-soluble substance as the core, by the fact that the surface of the microcapsule is uneven which results in enlarged surface areas, as compared to single-phase particles which possess smooth surface, etc., i.e., they are extremely useful from a diagnostic and preparative viewpoints.

This invention will now be described in detail with reference to the examples below, but is not deemed to be limited thereto.

Unless otherwise indicated, all percentages are by weight and all reactions were at room temperature and ambient pressure.

EXAMPLE 1

Preparation of microcapsules A Having Amino groups on the Surface Thereof

In an oil mixture (specific gravity, ca. 1.10) of 11.8 g. of diisopropylnaphthalene and 13.2 g. of chlorinated paraffin (degree of chlorination, 50%), 0.1 g of an oil-soluble red dyestuff, Eisen Sprion Red (made by Hodogaya Chemical Co., Ltd.) was dissolved. The resulting solution was then ice-cooled. 4 g. of a 50% methyl ethyl ketone solution of a tolylene diisocyanate-trimethylol propane adduct (tradename, Desmodur-L, made by Bayer Co., Ltd.) was dissolved in the thus cooled solution. The resulting oil solution was added to a solution of 2.5 g of hexamethylene diamine in 65 g. of a 5% aqueous solution of polyvinyl alcohol (degree of saponification, 88%; degree of polymerization, 500). The mixture was stirred and emulsified to adjust the average oil droplet size to about 6 μm. The emulsion was then diluted with 100 g. of water. The diluted emulsion was reacted at 75° C. for 1 hr. to effect microencapsulation.

After microcapsules were formed, the microcapsules slurry was centrifuged and washed with a saline solution to remove remaining reaction liquid. Thereafter, the microcapsules were dispersed in a saline solution to a solids content of 10%.

Preparation of Microcapsules B for Comparison

Microcapsules B were prepared in a manner similar to the above except that 0.1 g. of an ethylene diamine-propylene oxide adduct was used instead of hexamethylene diamine and dissolved in the same oil mixture as above having a specific gravity of 1.10.

Quantitative Determination of Concentration of Amino Groups on the Wall Surface of Microcapsules The microcapsules prepared described above were diluted with a saline solution to a solids content of 1%. After 100 μl of the thus diluted microcapsules was taken in a test tube, 1.5 ml. of a veronal buffer (pH 8.6) was added thereto. While vigorously stirring 0.5 ml. of a solution of 30 mg. of fluoresamine in 100 ml. of dioxane was dropwise added to the mixture. Using a fluorospectrometer made by Hitachi Ltd. as earlier discussed, the fluorescent intensity emitted was measured at Ex=390 nm and Em=475 nm. Using a calibration curve prepared from a glycine solution, the concentration of amino groups were quantitatively determined.

The invention microcapsules A prepared as above contained $5.6 \times 10^{-9}$ mol of amino groups per 1 mg. of solids content (core and wall materials; hereafter the same). On the surface of a microcapsule particle having an average size of 6 μm amino groups were present in a concentration of $3.7 \times 10^{-14}/cm^2$.

On the other hand, the amino groups in the microcapsules B for comparison were present in an amount less than $10^{-10}$ mole per 1 mg of solids content.

Sensitization of Microcapsules A having Amino Groups with Modified Human IgG

A 1.5 g. sample of each of the microcapsules prepared in accordance with Example 1 was taken and dispersed in 10 ml. of a saline solution, respectively. The dispersion was mixed with 100 μl. of glutaraldehyde and the mixture then reacted for 30 mins. at 37° C. After completion of the reaction, the reaction mixture was washed three times with a saline solution using a centrifuge and the resulting precipitate dispersed in 10 ml. of a saline solution.

The dispersion was then diluted to a 20-fold volume with a 1% saline solution of human IgG. A 2 ml. sample of the dilution product was added to 2 ml. of the aforesaid glutaraldehyde-treated microcapsule solution. The mixture was incubated for 1 hr. at 37° C., and then allowed to stand for 15 hrs. at 4° C. Thereafter, the mixture was twice subjected to centrifugal separation with a 0.2% glycine-containing saline solution. The thus washed product was dispersed in 2 ml. of a 0.15M phosphate- buffer saline solution (PBS, pH=7.2) containing 3% bovine serum albumin and 1% succharose to obtain a reagent A1 for detecting a rheumatism factor.

Comparison Example 1

Reagent A2 for comparison was prepared by a sensitization procedure as above except that sensitization was effected with modified human IgG without glutaraldehyde treatment.

Comparison Example 2

Using the microcapsules B for comparison obtained as above the same procedure as in Reagent A1 was repeated to sensitize with modified human IgG. Thus, Reagent B1 for comparison was prepared.

Microplate Test

With respect to reagents sensitized with modified human IgG, a cell in which agglutination could be clearly observed was judged to be positive, and the maximum dilution of sera giving a positive response was determined and made an antibody titer.

A serial dilution was prepared in respective cells on a microplate by diluting a 25 µl sample of sera of a positive control (patient's sera) for detecting rheumatism factor and of a negative control (normal rabbit sera) with a 0.15M phosphate buffer saline solution (PBS, pH=7.2) at a 2-fold dilution.

Thereafter, 25 µl of the microcapsule reagents sensitized with modified human IgG was taken by a dropper and dropwise added to the respective cells of the serially diluted sera on the microplate. The microplate was shaken for 5 mins. to cause an antigen-antibody reaction. Thereafter, the microplate was allowed to stand overnight in a refrigerator. The agglutination patterns formed at the bottom of the cells were observed the next morning to obtain the titer values shown in Table 1 below.

TABLE 1

| Reagent | Antibody Titer | |
|---|---|---|
| | Positive Serum | Negative Serum |
| Reagent $A_1$ | 2,560 | $\leq 20$ |
| Reagent $A_2$ for comparison | 320 | $\leq 20$ |
| Reagent $B_1$ for comparison | 40 | $\leq 20$ |

From the results shown above, it can be understood that the reagent obtained by sensitizing the microcapsule having amino groups on the surface thereof with modified human IgG provides higher sensitivity for detecting rheumatism factor by $2^6$ times than that of Reagent $B_1$ for comparison It is also easily understood that the stronger binding of modified human IgG onto the surface of the microcapsules provides higher detection sensitivity since the system of the present invention is higher in detection sensitivity by $2^3$ times than that of Reagent $A_2$ for comparison.

Adaptability to Freeze-Drying

The reagents sensitized with modified human IgG prepared as above were freeze-dried using a freeze-drying machine, Model FD-1 (tradename, manufactured by Tokyo Rika Co., Ltd.). After allowing the thus freeze-dried reagents to stand for 1 week at 4° C. in a refrigerator, the moisture corresponding to that removed by drying was freshly added to the restore the same to their original state. The microplate test as described above was performed to obtain antibody titer values as shown in Table 2 below.

TABLE 2

| Reagent | Antibody Titer | |
|---|---|---|
| | Positive Serum | Negative Serum |
| Reagent $A_1$ of Invention: Freeze-dried | 1,280 | $\leq 20$ |
| Reagent $A_2$ for comparison: Freeze-dried | 40 | $\leq 20$ |
| Reagent $B_1$ for comparison: Freeze-dried | $\leq 20$ | $\leq 20$ |

As is seen from the results shown in the table above, the reagent obtained by chemically binding modified human IgG to the microcapsules having amino groups on the wall surface thereof could indicate almost the same antibody titer even after freeze-drying, but the antibody titer was seriously reduced in the reagents for comparison in which modified human IgG was not chemically bound to the microcapsule wall so that the reagents for comparison could not withstand actual use.

EXAMPLE 2

Preparation of Microcapsule Having Carboxy Groups on the Surface Thereof

Microcapsules were prepared under conditions as in Example 1 except that 3 g. of carboxymethyl cellulose was dissolved in the aqueous solution of polyvinyl alcohol instead of hexamethylene diamine.

Quantitative Determination of Carboxy Groups on the Wall Surface of Microcapsules One of the two functional groups of carbodiimide was reacted with carboxy groups on the wall surface of the microcapsules. Next, ethylenediamine was reacted with the other unreacted functional group of the carbodiimide. Thus, the carboxy groups were converted into amino groups, whereafter the concentration of which amino groups were quantitatively determined in accordance with the method described in Example 1. That is, a 1.5 g. sample of the thus prepared microcapsules was taken and diluted in 10 ml. of a 0.15M phosphate buffer having a pH of 4.5. 5 ml. of a 1% aqueous solution of 1-ethyl-3-(3,3-dimethylaminopropyl)carbodiimide hydrochloride was added to the resulting silution. The mixture was then incubated for 1 hr. at 37° C. After the remaining reaction solution was removed by centrifugal separation, the precipitate was dispersed in 10 ml. of a 0.1% ethylene diamine solution. The resulting dispersion was incubated at 37° C. for 1 hr.

After completion of the reaction, the remaining liquid was removed by centrifuging and the precipitate was dispersed in 15 ml. of a saline solution. From the dispersion, a 100 µl sample was taken up in a test tube and the concentration of amino groups was determined in accordance with the method described in Example 1.

In the case where the microcapsules prepared as above were treated with ethylene diamine, amino groups were present at $2.7 \times 10^{-8}$ mol/mg of the microcapsule solids content, i.e., carboxy groups of at least $2.7 \times 10^{-8}$ mol were present. Carboxy groups were thus present in a concentration of $1.9 \times 10^{15}/cm^2$ on the surface of a microcapsule particle having an average size of 6 µm.

Sensitization of Carboxy-Containing Microcapsule with Modified Human IgG

The microcapsules prepared in this Example 2 were taken with a dropper in 1.5 g. samples of each and dispersed in 10 ml. of a 0.15M phosphate buffer having a pH of 4.5. To the resulting dispersion, 2 ml. of a 1% aqueous solution of 1-ethyl-3-(3,3-dimethylaminopropyl)carbodiimide hydrochloride were added and the mixture was reacted at 37° C. for 60 mins. After completion of the reaction, the reaction mixture was washed three times with a saline solution by centrifugal separation. Thereafter, modified human IgG was sensitized in a manner as in Example 1 to prepare a reagent for detecting rheumatism factor.

Using the thus obtained reagent, a microplate test was performed as in Example 1 to obtain the antibody titer values given in the table below.

TABLE 3

| Reagent | Antibody Titer | |
|---|---|---|
| | Positive Sera | Negative Sera |
| Reagent of Invention obtained in this Example 2 | 2,560 | ≦20 |

EXAMPLE 3

Preparation of Microcapsules Having Hydroxy Groups on the Surface Thereof

Microcapsules having hydroxy groups on the wall surface thereof were prepared as in Example 1 except that 3 g. of polyvinyl alcohol (Poval, made by Kuraray Co., Ltd.; degree of saponification 90%; degree of polymerization 500) was dissolved in an aqueous solution of polyvinyl alcohol in place of hexamethylene diamine. Otherwise all conditions were identical with the preparation conditions of the microcapsules in Example 1.

Quantitative Determination of Hydroxy Groups Present on the Wall Surface of Microcapsules Cyanuric chloride was reacted with the hydroxy groups on the wall surface of the microcapsules. Then, ethylene diamine was reacted with remaining functional groups of the cyanuric chloride which were unreacted. The hydroxy groups were thus converted into amino groups and the concentration of the amino groups was then quantitatively determined in accordance with the method described in Example 1.

That is, 1.5 g. samples were taken from the microcapsules prepared in accordance with this Example 3 and diluted in 10 ml. of a 0.15M phosphate buffer solution having a pH of 8.0. 5 ml. of a 1% aqueous solution of cyanuric chloride was added to the diluted samples, respectively. The resulting mixture was then incubated at 37° C. for 2 hrs. After completion of the reaction, the remaining liquid was removed by centrifuging and the precipitate dispersed in 15 ml. of a saline solution. From the dispersion, a 100 μl sample was taken into a test tube. The concentration of the amino groups was measured in accordance with the method described in Example 1.

The microcapsules contained $1.1 \times 10^{-8}$ mol of amino groups per 1 mg. of the solids content of the microcapsules, i.e., at least $1.1 \times 10^{-8}$ mol of hydroxy groups per 1 mg. of solids content. The hydroxy groups were present on the surface of a microcapsule particle having an average size of 6 μm in a concentration of $7.3 \times 10^{14}/cm^2$.

Sensitive Microcapsules with Modified Human IgG Having Hydroxy Groups on the Surface Thereof From the microcapsules prepared in accordance with this Example 3, 1.5 g. samples were taken and dispersed in 10 ml. of a 0.15M phosphate buffer solution having a pH of 8.0. To the dispersion, 2 ml. of a .1% aqueous solution of cyanuric chloride was added. The mixture was reacted at 37° C. for 2 hrs. After completion of the reaction, the reaction product was washed three times with a saline solution by centrifugal separation. Thereafter, sensitization was performed with modified human IgG as per Example 1 to prepare a reagent for detecting rheumatism factor.

Using the thus prepared reagent, a microplate test was performed as per Example 1 to obtain the antibody titers shown in the table below.

TABLE 4

| Reagent | Antibody Titer | |
|---|---|---|
| | Positive Sera | Negative Sera |
| Reagent obtained in this Example 3 | 1,280 | ≦20 |

EXAMPLE 4

Preparation of Microcapsule Having Mercapto Groups

From the microcapsules prepared in accordance with Example 1, 5 g. was taken and dispersed in 20 ml. of a 0.15M phosphate buffer solution having a pH of 6.0. 5 ml. of a 1% aqueous solution of S-acetylmercaptosuccinic anhydride was added to the dispersion and the mixture was reacted at room temperature for 1 hr. After completion of the reaction, the remaining liquid was removed by centrifugal separation. Thereafter, the resulting solid product was dispersed in 25 ml. of a saline solution.

Quantitative Determination of Mercapto Groups Present on the Surface of Microcapsules Sampling was performed using 10 ml. of the microcapsules (solids content, 2%) with which the S-acetylmercaptosuccinic anhydride had been reacted.

Using a silver sulfide electrode based upon a saturated calomel electrode as the standard, the change in potential was read out with a pH meter manufactured by Hitachi-Horiba Co., Ltd., after dropwise adding 0.002N silver nitrate. When 0.41 ml. of silver nitrate had been added, the potential suddenly changed, that is, mercapto groups in an amount of $4.1 \times 10^{-9}$ mol were present per 1 mg. of the solids content of the microcapsules and mercapto groups of $2.7 \times 10^{14}/cm^2$ were present on the surface of a microcapsule particle having an average size of 6 μm.

Sensitization with Modified Human IgG

As per Example 1, 0.5 ml. of a 0.15M phosphate buffer solution having a pH of 6.5 was added to 1 ml. of a 1% aqueous solution of modified human IgG. While stirring with a stirrer, 2 mg. of S-acetylmercaptosuccinic anhydride were added to the mixture. The mixture was then reacted at room temperature for 40 mins. After completion of the reaction, the reaction mixture was passed through Sephadex G-25 column to separate low molecular weight substances. The total volume was made 20 ml., from which 2 ml. was taken and added to 2 ml. of the microcapsules prepared in accordance with Example 4. To this mixture, 2 ml. of o-phenylene dimaleimide dissolved in a 0.15M phosphate buffer solution (pH 7.0) was added to saturation. The mixture was then reacted for 1 hr. at 37° C. After completion of the reaction, the reaction product was settled at 4° C. for 15 hrs. Thereafter, the reaction product was centrifugally separated and washed with a saline solution and then dispersed in 2 ml. of a 0.15M phosphate buffer saline solution containing 3% bovine serum albumin to obtain a reagent for detecting rheumatism factor.

Using the thus obtained reagent, a microplate test was performed as per Example 1 to obtain the antibody titers shown in the table below.

TABLE 5

| Reagent | Antibody Titer | |
|---|---|---|
| | Positive Serum | Negative Serum |
| Reagent obtained in this Example | 2,560 | ≦20 |

While the invention has been described in detail and with reference to specific embodiments thereof, it will be apparent to one skilled in the art that various changes and modifications can be made therein without departing from the spirit and scope thereof.

What is claimed is:

1. Microcapsules for effecting an immune response which comprise a wall having an oily substance encapsulated therein as a core and an antigen or antibody bound to a functional group of the wall surface of the microcapsules via a cross linking agent, wherein the average particle size of the microcapsule is in the range of from 0.1 to 30 μm and the microcapsules have a variable specific gravity ranging from about 0.80 to about 1.20.

2. The microcapsules of claim 1 wherein said functional group is selected from the group consisting of an amino group, a carboxy group, a hydroxy group and a mercapto group.

3. The microcapsules of claim 1 wherein said wall is prepared by reacting a compound selected from the group consisting of a polyfunctional isocyanate, a polyfunctional isothiocyanate, a polyfunctional acid chloride and a polyfunctional epoxy compound with an aminocontaining substance selected from the group consisting of ethylenediamine, hexamethylene diamine, cyclic amines, arginine, lysine and cystine.

4. The microcapsules of claim 1 wherein said wall is prepared by reacting a compound selected from the group consisting of a polyfunctional isocyanate, a polyfunctional isothiocyanate, a polyfunctional acid chloride and a polyfunctional epoxy compound with a carboxy-containing substance selected from the group consisting of carboxymethyl cellulose, polyacrylic acid, polymethacrylic acid and polystyrene carboxylic acid.

5. The microcapsules of claim 1 wherein said wall is prepared by reacting a compound selected from the group consisting of a polyfunctional isocyanate, a polyfunctional isothiocyanate, a polyfunctional acid chloride and a polyfunctional epoxy compound with thiourea to form microcapsule walls and then reducing the thus formed microcapsules.

6. The microcapsules of claim 1 wherein said wall is prepared by reacting a compound selected from the group consisting of a polyfunctional isocyanate, a polyfunctional isothiocyanate, a polyfunctional acid chloride and a polyfunctional epoxy compound with an ester compound selected from the group consisting of a polyacrylate and a polymethacrylate to form the microccapsule wall, and then the microcapsule wall thus formed is hydrolyzed under acidic conditions.

7. The microcapsules of claim 3, 4, 5 or 6 wherein said polyfunctional isothiocyanate is selected from the group consisting of phenylene diisothiocyanate and ethylene diisothiocyanate.

8. The microcapsules of claim 3, 4, 5 or 6 wherein said polyfunctional isocyanate is selected from the group consisting of toluene diisocyanate, xylene diisocyanate, tolylene diisocyanate and hexamethylene diisocyanate.

9. The microcapsules of claim 3, 4, 5 or 6 wherein said polyfunctional acid chloride is 1-hydroxy-2,4-disulfonyl chloride.

10. The microcapsules of claim 3, 4, 5 or 6 wherein said polyfunctional epoxy compound is diepoxybenzene.

11. The microcapsules of claim 1 wherein said cross linking agent is employed in an amount of 5 to 25 wt% and a compound introducing said functional group into the microcapsule in a range of 2 to 20 wt%, based upon a core of the microcapsule.

12. The microcapsules of claim 1 wherein said functional group is present in a concentration of at least $10^{-9}$ mol. per 1 mg. of the solids content of the microcapsules.

13. The microcapsules of claim 12 wherein said functional group is present in a concentration of from $10^{-9}$ to $10^{-5}$ ml. per 1 mg. of solids content of the microcapsules.

14. The microcapsules of claim 1 wherein the cross linking agent is a compound selected from the group consisting of a dialdehyde, a diisocyanate, an amide ester, a disulfonyl chloride, a halonitrobenzene, a water-soluble carbodiamide, an isoxazolium salt, an alkyl chloroformate, a N,N'-o-phenylenedimaleimide ester or an m-maleimidobenzoyl-N-hydroxysuccinimide ester.

15. The microcapsules of claim 1 wherein the cross linking agent is a compound selected from the group consisting of glutaraldehyde, toluene-2,4-diisocyanate, p-phenylenedithioisocyanate, diethyl maloneimidate, 1-hydroxy-2,4-disulfonyl chloride, p,p'-difluoro-m,m'-dinitrophenylsulfonic acid, 1-ethyl-3-(3-dimethylaminopropyl)carbodiimide hydrochloride, 1-cyclohexyl-3-(2-morpholinyl-4-ethyl)carbodiimidomethyl-p-toluenesulfonic acid, N-ethyl-5-phenylisoxazolium-3'-sulfonic acid, and ethyl chloroformate.

16. The microcapsules of claim 1, having an average particle size of from 0.5 to 10 μm.

* * * * *